US011357724B2

(12) United States Patent
Pottier et al.

(10) Patent No.: US 11,357,724 B2
(45) Date of Patent: *Jun. 14, 2022

(54) PHARMACEUTICAL COMPOSITION, PREPARATION AND USES THEREOF

(71) Applicant: Curadigm SAS, Paris (FR)

(72) Inventors: Agnès Pottier, Paris (FR); Laurent Levy, Paris (FR); Marie-Edith Meyre, Saint Mande (FR); Audrey Darmon, Alfortville (FR); Matthieu Germain, Champigny sur Marne (FR)

(73) Assignee: CURADIGM SAS, Paris (FR)

( * ) Notice: Subject to any disclaimer, the term of this patent is extended or adjusted under 35 U.S.C. 154(b) by 19 days.

This patent is subject to a terminal disclaimer.

(21) Appl. No.: 16/554,765

(22) Filed: Aug. 29, 2019

(65) Prior Publication Data
US 2020/0009050 A1 Jan. 9, 2020

Related U.S. Application Data

(63) Continuation of application No. 14/892,271, filed as application No. PCT/EP2014/061296 on May 30, 2014, now Pat. No. 10,413,509.

(Continued)

(30) Foreign Application Priority Data

May 30, 2013 (EP) .................... 13305712

(51) Int. Cl.
*A61K 9/127* (2006.01)
*A61K 9/14* (2006.01)
(Continued)

(52) U.S. Cl.
CPC .......... *A61K 9/127* (2013.01); *A61K 9/0014* (2013.01); *A61K 9/1271* (2013.01); *A61K 9/14* (2013.01);
(Continued)

(58) Field of Classification Search
CPC ..................... A61K 9/127; A61K 9/1271
See application file for complete search history.

(56) References Cited

U.S. PATENT DOCUMENTS 4,280,918 A 7/1981 Homola et al.
6,160,006 A 12/2000 Edwards et al.
(Continued)

FOREIGN PATENT DOCUMENTS

CN 102532154 7/2012
EP 2 000 150 12/2008
(Continued)

OTHER PUBLICATIONS

Robert M. Abra, Mark E. Bosworth and C. Anthony Hunt. "Liposome Disposition in Vivo: Effects of Pre-Dosing with Liposomes." Research Communications in Chemical Pathology and Pharmacology, vol. 29, No. 2, Aug. 1980, pp. 349-360. (Year: 1980).*
(Continued)

*Primary Examiner* — Isaac Shomer
(74) *Attorney, Agent, or Firm* — Saliwanchik, Lloyd & Eisenschenk

(57) ABSTRACT

The present invention relates to a pharmaceutical composition comprising the combination of (i) a biocompatible nanoparticle and of (ii) a pharmaceutical compound of interest, to be administered to a subject in need of such a compound of interest, wherein the nanoparticle potentiates the compound of interest efficiency. The longest dimension of the biocompatible nanoparticle is typically between about 4 and about 500 nm, and its absolute surface charge value is of at least 10 mV (|10 mV|). The invention also relates to such a composition for use for administering the compound of interest to a subject in need thereof, wherein the nan-
(Continued)

oparticle and the compound of interest are to be administered to said subject between more than 5 minutes and about 72 hours from each other.

14 Claims, 3 Drawing Sheets

Related U.S. Application Data

(60) Provisional application No. 61/828,794, filed on May 30, 2013.

(51) Int. Cl.
    *A61K 9/51*         (2006.01)
    *A61K 31/704*     (2006.01)
    *A61K 9/00*         (2006.01)

(52) U.S. Cl.
    CPC .......... *A61K 9/5115* (2013.01); *A61K 31/704* (2013.01); *Y10S 977/773* (2013.01)

(56) References Cited

U.S. PATENT DOCUMENTS

| | | | |
|---|---|---|---|
| 6,686,332 B1 | 2/2004 | Van Leeuwan et al. | |
| 8,845,507 B2 | 9/2014 | Levy et al. | |
| 10,391,058 B2* | 8/2019 | Germain | A61P 35/00 |
| 10,413,509 B2* | 9/2019 | Pottier | A61K 9/5115 |
| 10,765,632 B2* | 9/2020 | Germain | A61K 47/6911 |
| 2002/0110586 A1* | 8/2002 | Madden | A61K 9/1272 |
| | | | 424/450 |
| 2003/0186869 A1* | 10/2003 | Poiani | A61K 47/60 |
| | | | 424/78.06 |
| 2004/0166060 A1* | 8/2004 | Sgouros | A61K 51/1234 |
| | | | 424/1.65 |
| 2005/0090732 A1* | 4/2005 | Ivkov | A61N 2/002 |
| | | | 600/411 |
| 2006/0264804 A1 | 11/2006 | Karmon et al. | |
| 2007/0036834 A1 | 2/2007 | Pauletti et al. | |
| 2007/0088414 A1* | 4/2007 | Campbell | B82Y 10/00 |
| | | | 607/101 |
| 2008/0187595 A1 | 8/2008 | Jordan et al. | |
| 2008/0193372 A1 | 8/2008 | Lanza et al. | |
| 2009/0092661 A1 | 4/2009 | Huang et al. | |
| 2011/0027375 A1 | 2/2011 | Tillement et al. | |
| 2011/0207221 A1* | 8/2011 | Cost | C12N 9/22 |
| | | | 435/440 |
| 2011/0213192 A1 | 9/2011 | Levy et al. | |
| 2012/0157509 A1 | 6/2012 | Hadwiger et al. | |
| 2012/0225128 A1 | 9/2012 | Jordan et al. | |
| 2014/0056813 A1 | 2/2014 | Pottier et al. | |
| 2014/0186447 A1 | 7/2014 | Desai | |
| 2014/0271489 A1 | 9/2014 | Grinstaff et al. | |
| 2016/0310614 A1 | 10/2016 | Pottier et al. | |
| 2017/0258717 A1 | 9/2017 | Germain et al. | |
| 2017/0258718 A1 | 9/2017 | Meyre et al. | |
| 2017/0258720 A1* | 9/2017 | Pottier | A61K 9/0019 |
| 2017/0258721 A1 | 9/2017 | Germain et al. | |
| 2017/0258937 A1 | 9/2017 | Meyre et al. | |

FOREIGN PATENT DOCUMENTS

| | | |
|---|---|---|
| EP | 2 537 530 | 12/2012 |
| FR | 2 922 106 | 4/2009 |
| JP | H10-120597 | 5/1998 |
| WO | WO 96/35415 | 11/1996 |
| WO | WO 99/08676 | 2/1999 |
| WO | WO 2005/063305 | 7/2005 |
| WO | WO 2005/086639 | 9/2005 |
| WO | WO 2007/116954 | 10/2007 |
| WO | WO 2007/128066 | 11/2007 |
| WO | WO 2009/081287 | 7/2009 |
| WO | WO 2009/105774 | 8/2009 |
| WO | WO 2009/142754 | 11/2009 |
| WO | WO 2009/147214 | 12/2009 |
| WO | WO 2010/048623 | 4/2010 |
| WO | WO 2011/070324 | 6/2011 |
| WO | WO 2011/119988 | 9/2011 |
| WO | WO 2011/151631 | 12/2011 |
| WO | WO 2012/051220 | 4/2012 |
| WO | WO 2012/104275 | 8/2012 |
| WO | WO 2012/104277 | 8/2012 |
| WO | WO 2014/039874 | 3/2014 |
| WO | WO 2014/057432 | 4/2014 |
| WO | WO 2014/191569 | 12/2014 |
| WO | WO 2015/091888 | 6/2015 |

OTHER PUBLICATIONS

Robert A. Copeland, David L. Pompliano and Thomas D. Meek. "Drug-target residence time and its implications for lead optimization." Nature Reviews Drug Discovery, vol. 5, Sep. 2006, pp. 730-739 and one additional page. (Year: 2006).*
Reina E. Mebius and Georg Kraal. "Structure and Function of the Spleen." Nature Reviews Immunology, vol. 5, Aug. 2005, pp. 606-616. (Year: 2005).*
Sylvie Ponlot. https://www.technoflex.net/en/news/flexmag/flexmag-14/4-injection-methods-4-levels-of-action/ accessed Mar. 14, 2022, pp. 1-2. (Year: 2022).*
Bowen, P., "Particle Size Distribution Measurement from Millimeters to Nanometers and from Rods to Platelets," *Journal of Dispersion Science and Technology*, Jan. 1, 2002, vol. 23, No. 5, pp. 631-662.
Written Opinion in International Application No. PCT/EP2014/061296, dated Sep. 5, 2014, pp. 1-9.
Yu, S. et al. "Carboxyl group (-$CO_2H$) functionalized ferrimagnetic iron oxide nanoparticles for potential bio-applications" *Journal of Materials Chemistry*, 2004, pp. 2781-2786, vol. 14.
Ismail, M.F. et al. "Potential therapeutic effect of nanobased formulation of rivastigmine on rat model of Alzheimer's disease" *International Journal of Nanomedicine*, 2013, pp. 393-406, vol. 8.
Abu Lila, A. S. et al. "Oxaliplatin encapsulated in PEG-coated cationic liposomes induces significant tumor growth suppression via a dual-targeting approach in a murine solid tumor model" *Journal of Controlled Release*, 2009, pp. 8-14, vol. 137.
Gabizon, A. A. "Liposome circulation time and tumor targeting: implications for cancer chemotherapy" *Advanced Drug Delivery Reviews*, 1995, pp. 285-294, vol. 16.
Harashima, H. et al. "Size Dependent Liposome Degradation in Blood: In Vivo/In Vitro Correlation by Kinetic Modeling" *Journal of Drug Targeting*, 1995, pp. 253-261, vol. 3.
Hadaruga, D. I. et al. "Liposomes containing titanium dioxide nanoparticles (Short communication)" *Journal of Agroalimentary Processes and Technologies*, 2010, pp. 62-66, vol. 16, No. 1.
Shamsipour, F. et al. "Conjugation of Monoclonal Antibodies to Super Paramagnetic Iron Oxide Nanoparticles for Detection of her2/neu Antigen on Breast Cancer Cell Lines" *Journal of Medical Biotechnology*, Apr.-Jun. 2009, pp. 27-31, vol. 1, No. 1.
Kim, J.-Y. et al. "In-vivo tumor targeting of pluronic-based nanocarriers" *Journal of Controlled Release*, 2010, pp. 109-117, vol. 147.
Yu, M. K. et al. "Drug-Loaded Superparamagnetic Iron Oxide Nanoparticles for Combined Cancer Imaging and Therapy In Vivo" *Angew. Chem. Int. Ed.*, 2008, pp. 5362-5365, vol. 47.
Choi, W. I. et al. "The effect of mechanical properties of iron oxide nanoparticle-loaded functional nano-carrier on tumor targeting and imaging" *Journal of Controlled Release*, 2012, pp. 267-275, vol. 162.
Liang, X. et al. "Mechanical properties and stability measurement of cholesterol-containing liposome on mica by atomic force microscopy" Journal of Colloid and Interface Science, 2004, pp. 53-62, vol. 278.
Nie, Y. et al. "Cholesterol Derivatives Based Charged Liposomes for Doxorubicin Delivery: Preparation, In Vitro and In Vivo Characterization" *Theranostics*, 2012, pp. 1092-1103, vol. 2, No. 11.

(56) References Cited

OTHER PUBLICATIONS

Bhatt, N. et al. "Stability study of O/W emulsions using zeta potential" *Journal of Chemical and Pharmaceutical Research*, 2010, pp. 512-527, vol. 2, No. 1.
Thongborisute, J. et al. "Properties of Liposomes coated with hydrophobically modified chitosan in oral liposomal drug delivery" *Pharmazie*, 2006, pp. 106-111, vol. 61.
Ogu, C. C. et al. "Drug interactions due to cytochrome P450" *BUMC Proceedings*, Oct. 2000, pp. 421-423, vol. 13.
DeKrafft, K.E. et al. "Zr- and Hf-based nanoscale metal-organic frameworks as contrast agents for computed tomography" *Journal of Materials Chemistry*, Sep. 21, 2012, pp. 18139-18144, vol. 22, No. 35.
Maggiorella, L. et al. "Nanoscale radiotherapy with hafnium oxide nanoparticles" *Future Oncology*, Sep. 1, 2012, pp. 1167-1181, vol. 8, No. 9.
Written Opinion in International Application No. PCT/EP2014/078619, dated Mar. 26, 2015, pp. 1-6.
Babcock, J. J. et al. "Bovine serum albumin oligomers in the E- and B-forms at low protein concentration and ionic strength" *International Journal of Biological Macromolecules*, Feb. 1, 2013, pp. 42-53, vol. 53.
Ma, P. et al. "Paclitaxel Nano-Delivery Systems: A Comprehensive Review" *Journal of Nanomedicine and Nanotechnology*, Jan. 1, 2013, pp. 1-16, vol. 4, No. 2.
Written Opinion in International Application No. PCT/EP2015/077423, dated Jan. 21, 2016, pp. 1-5.
He, C. et al. "Effects of particle size and surface charge on cellular uptake and biodistribution of polymeric nanoparticles" *Biomaterials*, May 1, 2010, pp. 3657-3666, vol. 31, No. 13.
"NCL Method PCC-2 Measuring Zeta Potential of Nanoparticles" Nov. 1, 2009, Retrieved from the Internet: URL:http://ncl.cancer.gov/NCL_Method_PCC-2.pdf on Feb. 23, 2015, pp. 1-14.
Written Opinion in International Application No. PCT/EP2015/077446, dated Feb. 3, 2016, pp. 1-6.
Banquy, X. et al. "Effect of mechanical properties of hydrogel nanoparticles on macrophage cell uptake" *Soft Matter*, Jan. 1, 2009, pp. 3984-3991, vol. 5, No. 20.
Written Opinion in International Application No. PCT/EP2015/077438, dated Jan. 27, 2016, pp. 1-7.
Written Opinion in International Application No. PCT/EP2015/077425, dated Jan. 15, 2016, pp. 1-6.
Belisario, M. A. et al. "Effect of avarol, avarone and nine of their natural and synthetic derivatives on microsomal drug-metabolizing enzymes" *Toxicology Letters*, 1991, pp. 183-193, vol. 57.
Michalets, E. L. et al. "Update: Clinically Significant Cytochrome P-450 Drug Interactions" *Pharmacotherapy*, 1998, pp. 84-112, vol. 18, No. 1.
Written Opinion in International Application No. PCT/EP2015/077441, dated Feb. 3, 2016, pp. 1-6.
Hu, C.-M. J. et al. "Therapeutic Nanoparticles to Combat Cancer Drug Resistance" *Current Drug Metabolism*, 2009, pp. 836-841, vol. 10.
Abra, R.M. et al. "Liposome Disposition in Vivo: Effects of Pre-Dosing with Liposomes" *Research Communications in Chemical Pathology and Pharmacology*, Aug. 1980, pp. 349-360, vol. 29, No. 2.
Olson, F. et al. "Preparation of Liposomes of Defined Size Distribution by Extrusion Through Polycarbonate Membranes" *Biochimica et Biophysica Acta*, 1979, pp. 9-23, vol. 557.
Lu, H. et al. "Drug-target residence time: critical information for lead optimization" *Current Opinion in Chemical Biology*, 2010, pp. 467-474, vol. 14.
Copeland, R. A. et al. "Drug-target residence time and its implications for lead optimization" *Nature Reviews/Drug Discovery*, Sep. 2006, pp. 730-739, Corrigendum (1 page), vol. 5.
Simoes, S. et al. "Cationic liposomes for gene delivery" *Expert Opinion in Drug Delivery*, 2005, pp. 237-254, vol. 2, No. 2.
Singh, R. et al. "Nanoparticle-based targeted drug delivery" *Experimental and Molecular Pathology*, 2009, pp. 215-223, vol. 86.
Lai, B.-H. et al. "Surface modification of iron oxide nanoparticles with polyarginine as a highly positively charged magnetic nano-adsorbent for fast and effective recovery of acid proteins" *Process Biochemistry*, 2012, pp. 799-805, vol. 47.
Colbern, G. T. et al. "Significant Increase in Antitumor Potency of Doxorubicin HCl By Its Encapsulation in Pegylated Liposomes" *Journal of Liposome Research*, 1999, pp. 523-538, vol. 9, No. 4.
Yong, S.-B. et al. "Mononuclear phagocytes as a target, not a barrier, for drug delivery" *Journal of Controlled Release*, 2017, pp. 53-61, vol. 259.
Kiani, J. et al. "Medicinal importance of grapefruit juice and its interaction with various drugs" *Nutrition Journal*, 2007, pp. 1-9, vol. 6, No. 33.
Ohta, T. et al. "Paradisin C: a new CYP3A4 inhibitor from grapefruit juice" *Tetrahedron*, 2002, pp. 6631-6635, vol. 58.
UChicago News "Grapefruit juice boosts drug's anti-cancer effects" Obtained from internet on Oct. 23, 2018, originally published on Apr. 20, 2009, https://news.uchicago.edu/story/grapefruit-juice-boosts-drugs-anti-cancer-effects, pp. 1-4.
Uesawa, Y. et al. "Relationship between Lipophilicities of 1,4-Dihydropyridine Derivatives and Pharmacokinetic Interaction Strengths with Grapefruit Juice" *The Pharmaceutical Society of Japan*, 2008, pp. 117-122, vol. 128, No. 1.
Souhami, R. L. et al. "The Effect of Reticuloendothelial Blockade on the Blood Clearance and Tissue Distribution of Liposomes" *Biochimica et Biophysica Acta*, 1981, pp. 354-371, vol. 674.
Ginn, S.L. et al. "Gene therapy clinical trials worldwide to 2017: An update" *J. Gene Med.*, 2018, pp. 1-16, vol. 20.
Saunders, N.R.M. et al. "A Nanoprimer to Improve the Systemic Delivery of siRNA and mRNA" *Nano Lett.*, 2020, pp. 4264-4269, vol. 20.
Jadapalli, J. K. et al. "Doxorubicin triggers splenic contraction and irreversible dysregulation of COX and LOX that alters inflrmmation-resolution program in the mycocardium" *Am J Physiol Heart Circ. Physiol.*, 2018, pp. 1-31, vol. 315, No. 5.
Liang, X. et al. "Clinical Evaluations of Toxicity and Efficacy of Nanoparticle-Mediated Gene Therapy" *Human Gene Therapy*, Jun. 12, 2018, pp. 1227-1234, vol. 29, No. 11.
Miller, K. K. et al. "Chemotherapy-induced hand-foot syndrome and nail changes: A review of clinical presentation, etiology, pathogenesis, and management" *J Am Acad Dermatol*, 2014, pp. 1-8, vol. 71, No. 4.

\* cited by examiner

PHARMACEUTICAL COMPOSITION, PREPARATION AND USES THEREOF

CROSS-REFERENCE TO RELATED APPLICATIONS

This application is a continuation of U.S. application Ser. No. 14/892,271, filed Nov. 19, 2015, which is the U.S. national stage application of International Patent Application No. PCT/EP2014/061296, filed May 30, 2014, which claims the benefit of U.S. Provisional Patent Application No. 61/828,794, filed May 30, 2013.

FIELD OF THE INVENTION

The invention relates to a pharmaceutical composition comprising the combination of (i) a biocompatible nanoparticle and (ii) a compound of interest, to be administered to a subject in need of such a compound, wherein the nanoparticle potentiates the compound efficiency. The longest dimension of the biocompatible nanoparticle is typically between about 4 and about 500 nm, and its absolute surface charge value is of at least 10 mV (|10 mV|).

The invention also relates to such a composition for use for administering the compound of interest to a subject in need thereof, wherein the nanoparticle and the compound of interest are to be administered to said subject sequentially, typically between more than 5 minutes and about 72 hours from each other.

The combined, and typically sequential, administration to the subject of the biocompatible nanoparticle and of the compound of interest maintains the pharmaceutical (i.e. therapeutic, prophylactic or diagnostic) benefit of said compound of interest for a reduced toxicity thereof for said subject, or increases its pharmaceutical benefit for an equivalent or reduced toxicity, when compared to the pharmaceutical benefit and toxicity induced by said compound when administered at the standard pharmaceutical dose.

The pharmaceutical composition of the invention typically allows a reduction of at least 10% of the administered compound pharmaceutical dose when compared to the standard pharmaceutical dose of said compound while maintaining the same pharmaceutical benefit for an equivalent toxicity, preferably a reduced toxicity, for the subject, or while increasing the pharmaceutical benefit for an equivalent or reduced toxicity for the subject.

BACKGROUND

In order to ensure safety and efficacy, therapeutic compounds are required to be selectively delivered to their target site at an optimal rate in the subject in need thereof.

Pharmacokinetics (pK) is a branch of pharmacology dedicated to the determination of the fate of substances administered externally to a living organism. This determination involves steps of measuring compound's concentrations in all major tissues over a long enough period of time, preferably until the compound's elimination. Pharmacokinetics is necessary to efficiently describe the compound's behavior in vivo, including the mechanisms of its absorption and distribution as well as its chemical changes in the organism. The pK profile in the blood can be fitted using various programs to obtain key pK parameters that quantitatively describe how the body handles the compound. Important parameters include maximum concentration ($C_{max}$), half-life ($t_{1/2}$), clearance, area under curve (AUC), and mean resident time (MRT), i.e. the average time during which a compound stays in an organism. When a prolonged blood circulation of the compound formulation is observed, it is usually associated with an increased $t_{1/2}$, a reduced clearance, an increased AUC, and an increased MRT. pK data are often used in deciding the optimal dose and dose regimen for maintaining the desirable blood concentration in order to improve therapeutics' efficiency with minimal side effects. In addition, as is well known by the skilled person, the blood concentration of a compound is correlated with both its efficacy and toxicity in most cases, typically for free drugs.

The physico-chemical properties of therapeutic as well as prophylactic compounds have an important impact on their pharmacokinetic and metabolic fate in the body. Therefore, selection of appropriate physico-chemical properties is key when designing such a compound. However, since the compound is not always endogenously provided by the organism itself and is usually externally administered, its biodistribution profile has to be optimized in order to fit with, and preferably optimize, the desired pharmacological action thereof.

Several approaches have been explored to optimize the delivery of a compound to its target site. A strategy is to design a therapeutic compound with stealth properties to prolong its blood half-life and, consequently, to enhance its accumulation to the target site. One favorable approach is the covalent attachment of polyethylene glycol (PEG) to the therapeutic compound that has proved to increase the in vivo half-life ($t_{1/2}$) of the circulating compound, the level of the in vivo half-life increase varying depending partly on the nature of the compound and on that of the coating. Also, drug carriers such as liposomes, emulsions or micelles have been developed to enhance therapeutic efficacy of drugs by modifying their biodistribution profile in the subject's body.

However, lack of selectivity in the biodistribution of the therapeutic compounds still remains a concern. So far, poor pharmacokinetics and high toxicity are important causes of failure in therapeutic compound development.

As an example, in the context of cancer treatment, intentional inhibition of essential functions of the body in order to kill cancer cells results in on-target or on-mechanism toxicity in normal cells, and clinicians have to rely on differences in dose-response and therapeutic compound distribution between tumors and normal tissues to find a possible therapeutic window. Of note, hepatotoxicity remains a major reason for drug withdrawal from pharmaceutical development and clinical use due to direct and indirect mechanisms of drug-induced cell injury in the liver.

An approach proposed for nanoparticulate compounds such as drug carriers [*Critical Reviews in Therapeutic Drug Carrier Systems* 11(1):31-59 1994] is to pre-inject a decoy carrier to decrease, saturate, or even inactivate the phagocytic capacity of the reticuloendothelial system (RES). Impairment or blockade may also be associated with decreased plasma levels of opsonic molecules. Intravenous administration of certain agents, such as alkyl esters of fatty acids, dextran sulfate, salts of rare earth elements (e.g. $GdCl_3$), or drug carriers, either empty or encapsulating clodronate, prior to administration of test particles has been demonstrated to induce moderate to dramatic reduction in Kupffer cells uptake.

For instance, the authors of "*Biomimetic amplification of nanoparticle homing to tumors*" [*PNAS* 2007], reported the role of RES in the clearance of their nanoparticles "CREKA-SPIO". Initial experiments showed that intravenous (IV) injected "CREKA-SPIO" nanoparticles did not effectively accumulate in MDA-MB-435 breast cancer xenografts. In contrast, a high concentration of particles was seen in RES tissues. By depleting RES macrophages in the liver with liposomal clodronate, they found a 5-fold prolongation of their particle's half-life. However, clodronate agent induces the apoptosis of macrophages from liver and spleen, and this is considered globally detrimental as macrophage depletion increases the risks associated with immunosuppression and infection. In a second experiment, the authors tested liposomes coated with chelated Ni (II) as a potential decoy particle hypothesizing that iron oxide and Ni (II) would attract similar plasma opsonins, and that Ni-liposomes could therefore deplete them in the systemic circulation. Indeed, intravenous (IV) injected Ni-liposomes, whether administered 5 minutes or 48 hours before the injection of CREKA-SPIO nanoparticles, allow a five-fold increase of the nanoparticles' blood half-life. However, high toxicity was observed causing deaths among tumor mice. Plain liposomes were also tested instead of Ni-liposomes. However, while reducing the toxicity when compared to said Ni-liposomes, plain liposomes were far less effective than them. Indeed, the blood half-life increase was only by a factor of about 2.

WO2005086639 relates to methods of administering a desired agent selectively to a target site in a subject, typically in the context of ultrasound or X-ray exposure, or in the context of magnetic resonance imaging (MRI), as well as in the context of therapy. The aim of the described method is to improve or maintain the efficiency of the agent of interest while reducing the total dose of agents concretely administered thanks to concomitant administration of a decoy inactive carrier.

The described invention employs a probability-based approach. A non-targeted inactive agent ("inactive carrier") is co-administered (i.e. "substantially simultaneously") with a targeted agent of interest (present in an "active composition") exhibiting similar physical features, in order to facilitate the evasion of the RES system by the targeted agent of interest thereby allowing an improved uptake of the agent of interest at the desired site. This approach results in a lower exposure of patients to the agent of interest and, as a consequence, in a lower per dosage cost of said agent of interest. The active composition and the decoy inactive carrier are administered within five minutes of each other, preferably within 2 minutes of each other, or even less. This approach relies on the presence of a large excess of untargeted "carrier" or "decoy" vehicles and on the probability that this decoy carrier in excess will compete with the targeted agent of interest for an uptake by the reticuloendothelial system when supplied in the presence of vehicles that are targeted to a desired location. The half-life of particles captured by RES is dose dependent, i.e. the circulating half-life of particles increases as the dosage increases. The slower clearance associated with higher dosages is thought to favor the maintaining of a total agents high concentration allowing a decrease of the dose of the agent of interest which is to be administered. In other words, an increased half-life of total agents due to a global higher dosage thereof should be beneficial to the targeted agents, according to the authors of WO2005086639. The requirement involved by this approach is that the active agent and the inactive one behave similarly with regard to their clearance characteristics in the RES, whatever their respective compositions.

In this approach, the quasi-concomitant injection of the inactive agent and of the active one is required to increase the global amount of agents present in the blood and consequently to prolong their blood half-life. Such strategy, which expressly relies on a probability-based approach, necessarily requires the association of the active agent with a targeting agent in order to achieve its successful accumulation on the target site by conferring said active agent an advantage over the inactive one. In addition, due to the quasi-concomitant injection, a specific design of the inactive carrier may be required depending on the intended use of the active composition.

As is apparent from the prior art, and despite of a long medical need, the improvement of compounds (including therapeutic and prophylactic as well as diagnostic compounds) which cannot be efficiently used in patients due to their unacceptable toxicity or to their unfavorable pharmacokinetics parameters remains a concern.

DETAILED DESCRIPTION

The present invention now allows optimization of the efficiency of a compound of interest (herein also simply identified as "the compound") whatever its intended use in the context of therapy, prophylaxis or diagnostic. The composition herein described which is a combination of (i) a biocompatible nanoparticle and of (ii) at least one compound of interest, optimizes the at least one compound of interest pharmacokinetic parameters, and, as a consequence, now renders possible the development of therapeutic compounds which could not have been developed otherwise due for example to their unacceptable toxicity.

A typical composition of the invention (herein generally identified as "pharmaceutical composition") is a composition comprising the combination of (i) a biocompatible nanoparticle and (ii) at least one compound ("the compound of interest"), wherein the longest dimension of the biocompatible nanoparticle is typically between about 4 nm and about 500 nm, and the absolute surface charge value of the biocompatible nanoparticle is of at least 10 mV.

A preferred object of the invention is a pharmaceutical composition comprising the combination of (i) a biocompatible nanoparticle and of (ii) a pharmaceutical compound of interest, wherein the longest dimension of the biocompatible nanoparticle is between about 4 nm and about 500 nm, and the absolute surface charge value of the biocompatible nanoparticle is of at least 10 mV mV|) for use for administering the pharmaceutical compound of interest to a subject in need thereof, wherein the nanoparticle and the compound of interest are to be administered to a subject in need of said compound of interest between more than 5 minutes and about 72 hours from each other.

The combined administration to the subject of the biocompatible nanoparticle and of the compound of interest, through the composition of the invention, typically allows (maintains) the same pharmaceutical (i.e. therapeutic, prophylactic or diagnostic) benefit of the compound with a reduced toxicity thereof for the subject, or increases the pharmaceutical benefit of the compound with an equivalent or reduced toxicity thereof for the subject (preferably a reduced toxicity), when compared to pharmaceutical benefit and toxicity induced by the standard pharmaceutical dose of said compound.

The pharmaceutical composition of the invention typically allows a reduction of at least 10%, preferably at least 15%, of the administered compound pharmaceutical (i.e. therapeutic, prophylactic or diagnostic) dose when compared to the standard pharmaceutical dose of said compound (i) while maintaining the same pharmaceutical benefit for an equivalent toxicity, preferably a reduced toxicity, for the subject or (ii) while increasing the pharmaceutical benefit for an equivalent or reduced toxicity for the subject.

As the shape of the particle can influence its "biocompatibility", particles having a quite homogeneous shape are herein preferred. For pharmacokinetic reasons, nanoparticles being essentially spherical, round or ovoid in shape are thus preferred. Such a shape also favors the nanoparticle interaction with or uptake by cells. Spherical or round shape is particularly preferred.

In the spirit of the invention, the term "nanoparticle" refers to a product, in particular a synthetic product, with a size in the nanometer range, typically between about 1 nm and about 500 nm, preferably between about 4 nm and about 500 nm, between about 4 and about 400 nm, about 30 nm and about 300 nm, about 20 nm and about 300 nm, about 10 nm and about 300 nm, for example between about 4 nm and about 100 nm, for example between about 10 nm, 15 nm or 20 nm and about 100 nm, or between about 100 nm and about 500 nm, typically between about 100 nm and about 300 nm.

The terms "size of the nanoparticle", "largest size of the nanoparticle" and "longest size of the nanoparticle" herein typically refer to the "longest or largest dimension of the nanoparticle" or "diameter of the nanoparticle" when spheroid or ovoid in shape. Transmission Electron Microscopy (TEM) or Cryo-TEM can be used to measure the size of the nanoparticle. As well, Dynamic Light Scattering (DLS) can be used to measure the hydrodynamic diameter of nanoparticles in solution. These two methods may further be used one after another to compare size measurements and confirm said size. A preferred method is DLS (Ref. International Standard IS022412 Particle Size Analysis—Dynamic Light Scattering, International Organisation for Standardisation (ISO) 2008).

To be usable in the context of the invention, the absolute electrostatic surface charge (also herein identified as "charge" or "surface charge") of the biocompatible nanoparticle is to be higher than |10 mV| (absolute value). The surface charge of a nanoparticle is typically determined by zeta potential measurements in an aqueous medium for a nanoparticle concentration between 0.2 and 10 g/L, for a pH between 6 and 8, and typically for electrolyte concentrations in the aqueous medium between 0.001 and 0.2 M, for example, 0.01 M or 0.15 M.

Typically, the biocompatible nanoparticle of the present invention has an electronic surface charge of at least |10 mV|, i.e. below −10 mV or above +10 mV, for example below between −12 mV or −15 mV and −20 mV or above between +12 mV or +15 mV and +20 mV, typically below −15 mV or above +15 mV. Preferably, the biocompatible nanoparticle of the present invention has an absolute electronic surface charge value ("absolute surface charge value") of more than 10 mV, said charge being even more preferably a negative charge.

So long as it is charged, the nanoparticle usable in the context of the invention can be either organic or inorganic. A mixture of organic and inorganic nanoparticles can further be used.

When organic, the nanoparticle can be a lipid-based nanoparticle (glycerolipid, phospholipid, sterol lipid, etc.), a protein-based nanoparticle also herein identified as "protein-nanoparticle" (albumin for instance), a polymer-based nanoparticle ("polymeric nanoparticle"), a co-polymer-based nanoparticle ("co-polymeric nanoparticle"), a carbon-based nanoparticle, a virus-like nanoparticle (for example a viral vector).

The organic nanoparticle may further be a nanosphere (plain nanoparticle) or a nanocapsule (hollow nanoparticle) such as a liposome, a gel, a hydrogel, a micelle, a dendrimer, etc. A mixture of the herein described organic nanoparticles can also be used.

The polymer or co-polymer can be of natural or synthetic origin.

Examples of synthetic (artificial) and natural polymers or co-polymers usable in the context of the invention to prepare organic nanoparticles can be selected from polylactic acid (PLA), Poly(lactide-co-glycolic) acid (PLGA), Polyethyleneglycol (PEG), Polyglactin, Polylactide, Polyoxyethylene fatty acid esters, Polypropylene glycol, Polysorbate, Polyvinyl alcohol, Polyacrylamide, Polymethylmethacrylate, Polyalkylcyanoacrylate, Polylactate-co-glycolate, Poly (amido amine), Poly(ethyleneimine), alginate, cellulose and cellulose derivatives, polymers, collagen, hyaluronic acid, polyglutamic acid (PGA), actin, polysaccharide, and gelatin.

When inorganic and when its longest dimension is typically below about 10 nm, for example below about 8 nm, below about 7 nm, typically comprised between about 7 nm and about 4 nm, for example below about 6 nm, below about 5 nm or below about 4 nm, the nanoparticle may be made of any inorganic material. The inorganic material may for example comprise metallic element from period 3, 4, 5, 6 of the Mendeleev's periodic table, including the lanthanides. When the longest dimension of the nanoparticle is typically below about 10 nm, the nanoparticles may assemble in larger structures. Assembling of nanoparticles in larger structure may typically be triggered by interactions between nanoparticles and a biocompatible polymer(s), protein(s), etc. Larger structure may also be obtained by trapping the nanoparticles in a carrier, typically a plain carrier such as gelatin structure (also herein identified as "gelatin nanoparticle") or a hollow carrier such as liposome. After in vivo administration, those larger structures may further release the nanoparticles.

When inorganic and when the longest dimension of said nanoparticle is typically of at least 10 nm, typically between 10 and 500 nm, the nanoparticle may comprise at least one of or may consist of (i) one or more divalent metallic elements selected for example from Mg, Ca, Ba and Sr, (ii) one or more trivalent metallic elements selected for example from Fe and Al, and (iii) one or more tetravalent metallic elements comprising Si.

In a particular embodiment, the inorganic material of the nanoparticle is selected from (i) one or more divalent metallic elements selected for example from Mg, Ca, Ba and Sr (ii) one or more trivalent metallic elements selected for example from Fe and Al and (iii) one or more tetravalent metallic elements comprising Si.

In a further particular embodiment, the inorganic material of the nanoparticle is selected from calcium carbonate ($CaCO_3$), magnesium carbonate ($MgCO_3$), magnesium hydroxide ($Mg(OH)_2$), iron hydroxide ($Fe(OH)_2$), iron oxyhydroxide (FeOOH), iron oxide ($Fe_3O_4$ or $Fe_2O_3$), aluminium oxide ($Al_2O_4$), aluminium hydroxide ($Al(OH)_3$), aluminium oxyhydroxide (AlOOH) and silicon oxide ($SiO_2$).

The nanoparticles used in the herein described compositions are to be biocompatible, i.e. compatible with living tissues. When required by their composition, the nanoparticles are thus to be coated with a biocompatible material to become usable. In a particular embodiment of the invention, the herein mentioned nanoparticle is thus covered with a biocompatible coating.

The biocompatible material can be an agent allowing interaction with a biological target. Such an agent will typically bring a positive or a negative charge on the nanoparticle's surface when the absolute charge of the nanoparticle is of at least 10 mV.

An agent forming a positive charge on the nanoparticle's surface can be for example selected from aminopropyltriethoxisilane or polylysine. An agent forming a negative charge on the nanoparticle surface can be for example selected from a phosphate (for example a polyphosphate, a metaphosphate, a pyrophosphate, etc.), a carboxylate (for example citrate or dicarboxylic acid, in particular succinic acid) or a sulphate.

In a particular embodiment, as long as the absolute charge of the nanoparticle is of at least 10 mV (|10 mV|), the nanoparticle can be coated with a biocompatible material selected from an agent displaying a steric group. Such a group may be selected for example from polyethylene glycol (PEG); polyethylenoxide; polyvinyl alcohol; polyacrylate; polyacrylamide (poly(N-isopropylacrylamide)); polycarbamide; a biopolymer; a polysaccharide such as dextran, xylan and cellulose; collagen; a switterionic compound such as polysulfobetain; etc.

The biocompatible coating may advantageously be a "full coating" (complete monolayer). This implies the presence of a very high density of biocompatible molecules creating an appropriate charge on the all surface of the nanoparticle.

The biocompatible coating may further comprise a labelling agent, typically an agent allowing the visualisation of a color using standard imaging equipment.

The combined administration of the biocompatible nanoparticle together with the compound of interest maintains the pharmaceutical (i.e. therapeutic, prophylactic or diagnostic), typically therapeutic, benefit of the compound of interest for a reduced toxicity, or increases the pharmaceutical benefit of the compound for an equivalent or reduced toxicity, for the subject, typically when administered to the subject in need of the compound of interest between more than 5 minutes and about 72 hours from each other, when compared to pharmaceutical benefit and toxicity induced by the standard pharmaceutical, typically therapeutic, dose of said compound.

In a particular embodiment, the combined administration of the biocompatible nanoparticle and of the compound of interest allows a reduction of at least 10%, preferably at least 15%, of the administered compound therapeutic dose, typically when administered to the subject in need of the compound of interest, between more than 5 minutes and about 72 hours from each other, when compared to the standard therapeutic dose of said compound while maintaining the same therapeutic benefit for an equivalent toxicity or a reduced toxicity (preferably a reduced toxicity) of the compound for the subject; or while increasing the therapeutic benefit for an equivalent or reduced toxicity of the compound for the subject.

In a particular embodiment, nanoparticle(s) are administered with several compounds of interest, typically two compounds of interest.

The nanoparticle is preferably cleared from the subject to whom it has been administered typically within 1 hour and 6 weeks, for example 1 month (4 weeks), within 1 hour and 1 month, for example between 1 hour and 3 weeks, or between 1 hour and 2 weeks, or between 1 hour and 1 week, following its administration to a subject in need of the compound of interest.

The material constituting the nanoparticle (including its biocompatible coating when present) is important in determining the biopersistence of the nanoparticle. The nanoparticle may be regarded as biodegradable (when constituted for example by a biodegradable polymer such as PLGA or PLA), dissolvable (iron oxide for example) or non biodegradable and non dissolvable. Biodegradable and dissolvable nanoparticles facilitate rapid nanoparticle clearance from the subject.

Different molecules or agents can be used according to the present teaching as the at least one compound of interest, typically as the at least one pharmaceutical compound of interest, administered in combination with a biocompatible nanoparticle as described hereinabove. This compound may be a therapeutic, a prophylactic or a diagnostic compound as previously explained. It can be an organic compound or an inorganic compound.

Examples of organic compounds usable as the compound of interest can be selected from a biological compound, an antibody, an oligonucleotide, a synthesized peptide, a small molecule targeted therapeutic, a cytotoxic compound, and any corresponding prodrug or derivative thereof, etc.

In a particular embodiment, the compound of interest used in the context of the present invention is an organic compound preferably selected from a biological compound, a small molecule targeted therapeutic, and a cytotoxic compound. In another particular embodiment, the compound of interest is selected from an antibody, an oligonucleotide, and a synthesized peptide.

A biological compound is for instance an antibody, preferably a monoclonal antibody ("mAb"), such as infliximab, adalimumab, bevacizumab, rituximab, trastuzumab, ranibizumab, cetuximab, or panatimumab; a protein or a recombinant protein, such as enbrel (etanercept) or interferon beta-la; a peptide or a recombinant peptide such as insulin glargine or betaseron; a vaccine such as prevnar 13 or gardasil; a biosimilar such as epogin; an enzyme or a recombinant enzyme such as replagal or creon; etc.

An oligonucleotide is for instance an antisense oligonucleotide, an aptamer, such as mipomersen sodium or pursennid, etc.

A synthesized or artificial peptide such as glatiramer acetate or leuprolide acetate.

A small molecule targeted therapeutic generally inhibits enzymatic domains on mutated, overexpressed, or otherwise critical protein (potential target in the context of cancer treatment) within the malignant cells. Some therapeutic agents include those that target cell division (for example, an aurora-kinase inhibitor or a cyclin-dependent kinase inhibitor), as well as other biological mechanisms such as protein turnover and chromatin modification (for example a histone-deacetylase inhibitor). Small molecules targeted therapeutics are for instance imatinib, rapamycin, gefitinib, erlotinib, sorafenib, sunitinib, nilotinib, dasatinib, lapatinib, bortezomib, atorvastatin, etc.

A cytotoxic compound is for instance a DNA-modifying agent, such as an anthracycline (for example doxorubicine, daunorubicine, etc.), an alkylating agent (for example melphalan or temozolomide), as well as a drug interfering very precisely with defined physiological mechanisms such as microtubule polymerization (for example taxol), or metabolite synthesis (for example methotrexate). An activable cytotoxic compound is typically used in the context of Photodynamic Therapy (for example photofrin), and is to be activated by an external source such as a laser source to produce its therapeutic effect. Other cytotoxic compounds are typically selected from chemotherapeutic agents as herein described or as known by the skilled oncologist.

A prodrug (for instance capecitabine or irinotecan) is metabolized in its active form in vivo to produce its expected therapeutic effect.

Examples of inorganic compounds usable as the compound of interest can be selected from a transition metal coordination complex, a radiopharmaceutical compound, a nanoparticle, etc.

Transition metal coordination complexes offer potential advantages over the more common organic-based drugs, including a wide range of coordination numbers and geometries, accessible redox states, 'tune-ability' of the thermodynamics and kinetics of ligand substitution, as well as a wide structural diversity. Metal-based substances interact with cell molecular targets, affecting biochemical functions resulting in malignant cell destruction. Transition metal coordination complexes are typically cytotoxic agents (for instance, platinum coordination complexes: cisplatin, carboplatin, oxaloplatin, or ruthenium or gold coordination complexes) acting on DNA structures.

Radiopharmaceutical compounds emit radiations for diagnosis purposes or in order to selectively destroy malignant cells. Typical radiopharmaceuticals may contain for example strontium-89, thallium-201, techtenium-99, samarium-83, etc.

Nanoparticle may be selected typically from a metal oxide nanoparticle (see WO 2009/147214 and WO 2007/118884 for example), a metallic nanoparticle (gold, platinum or silver nanoparticle for instance), a metal sulfide nanoparticle ($Bi_2S_3$ for instance), and any mixture thereof (for example a gold nanoparticle covered with hafnium oxide material). The nanoparticle is for example a nanoparticle which can be activated via an external source such as an electromagnetic radiation source, a ultrasound source, or a magnetic source, etc.

The compound of interest, which is administered in combination with a biocompatible nanoparticle as described hereinabove (typically sequentially administered as herein described), may be encapsulated in a carrier or grafted (or bound) to such a carrier according to means known by the skilled person. A typical carrier is for example a liposome (such as DOXIL or ThermoDox which uses thermosensitive lipid), micelle, polymeric (or "polymer") carrier, hydrogel, gel, co-polymeric carrier, protein carrier, inorganic carrier.

The pharmaceutical composition of the invention (defined by the combination of the compound of interest and of the nanoparticle) can be used in many fields, particularly in human or veterinary medicine. This composition is typically for use in an animal, preferably in a mammal (for example in the context of veterinary medicine), even more preferably in a human being whatever its age or sex.

The pharmaceutical compositions of the invention can be used in cardiovascular diseases, Central Nervous System (CNS) diseases, gastrointestinal diseases, genetic disorders, hematological disorders, hormonal disorders, immunology, infectious diseases, metabolic disorders, musculoskeletal disorders, oncology, respiratory diseases, toxicology, etc. In a preferred embodiment, the pharmaceutical composition is used in cardiovascular diseases, CNS diseases, oncology, infectious diseases, metabolic disorders.

In the context of the present invention, the nanoparticle and the compound(s) ("compound(s) of interest") are advantageously to be administered to a subject in need of said compound between more than 5 minutes and about 72 hours from each other, typically between more than 5 minutes and about 24 hours, preferably between more than 5 minutes or 30 minutes and about 12 hours, in order to optimize the compound pharmaceutical efficacy.

In the present invention, when the nanoparticle and the compound(s) ("compound(s) of interest") are advantageously to be administered to a subject in need of said compound between more than 5 minutes and about 72 hours from each other, the absolute surface charge value of the biocompatible nanoparticle is of at least 10 mV mV|).

In a particular embodiment of the present invention, when the nanoparticle and the compound(s) ("compound(s) of interest") are advantageously to be administered to a subject in need of said compound between more than 5 minutes and about 24 hours from each other, the absolute surface charge value of the biocompatible nanoparticle is advantageously of at least 15 mV (|15 mV|).

In another particular embodiment of the present invention, when the nanoparticle and the compound(s) ("compound(s) of interest") are advantageously to be administered to a subject in need of said compound between more than 5 minutes and about 12 hours from each other, the absolute surface charge value of the biocompatible nanoparticle is advantageously of at least 20 mV (|20 mV|).

Also herein described is a method for treating a subject suffering from a disease such as those herein mentioned, wherein said method comprises administering to said subject a pharmaceutical composition of the invention, typically administering a biocompatible nanoparticle and at least one compound of interest as herein described. Any one of the nanoparticle or at least one compound of interest can be administered first to the subject as long as the biocompatible nanoparticle and the compound are administered between more than 5 minutes and about 72 hours from each other. Administration of any of said nanoparticle or at least one compound of interest can be a single administration of each, repeated administrations of each, for example several consecutive administrations of each. The biocompatible nanoparticle may be administered once and the at least one compound of interest may be administered more than once and vice versa.

In a particular embodiment, the biocompatible nanoparticle is at least administered at the beginning of a protocol comprising several administrations of a compound interest, i.e. at least at the first administration of said compound of interest and before or after the administration thereof.

In another particular embodiment, the biocompatible nanoparticle is not administered at the beginning of a protocol comprising several administrations of a compound interest and is not administered before the second or third administration of said compound of interest, and before or after the administration thereof.

In the context of these last two embodiments, the biocompatible nanoparticle can also be administered together (before or after as previously explained) with the compound of interest during part or all of the subsequent administrations of said compound of interest.

In a particular embodiment, the nanoparticle of the invention is administered to the subject before administration to said subject of the at least one compound of interest, typically between more than 5 minutes and about 72 hours before administration of the at least one compound of interest.

In this context, the term "nanoparticle" can more particularly refer to a product, in particular a synthetic product, with a size between about 4 nm and about 100 nm, for example between about 10 nm, 15 nm or 20 nm and about 100 nm. An example of a compound of interest to be used with such nanoparticles is an organic compound, typically a biological compound. It is advantageously selected from an antibody, an oligonucleotide, a synthesized peptide, a small molecule targeted therapeutic, and a cytotoxic compound and is preferably an antibody, a small molecule targeted therapeutic and/or a cytotoxic compound. The term "nanoparticle" can otherwise refer to a product, in particular a synthetic product, with a size between about 100 nm and about 500 nm, typically between about 100 nm and about 300 nm. An example of a compound interest to be used with such nanoparticles is an inorganic compound, typically selected from a metallic nanoparticle, a metal oxide nanoparticle, a metal sulfide nanoparticle and any mixture thereof or any compound of interest encapsulated in a carrier or grafted to such a carrier.

The biocompatible nanoparticle of the pharmaceutical composition of the invention can be administered by any route, such as intravenous (IV), intra-arterial, and/or intra-peritoneal. A preferred route of administration is the intravenous route.

The compound(s) of interest of the pharmaceutical composition of the invention can be administered by different routes, such as subcutaneous, intravenous (IV), intradermal, intra-arterial, airway (inhalation), intraperitoneal, intramuscular and/or oral (per os) routes.

The following examples illustrate the invention without limiting its scope.

EXAMPLES

Figure 1:
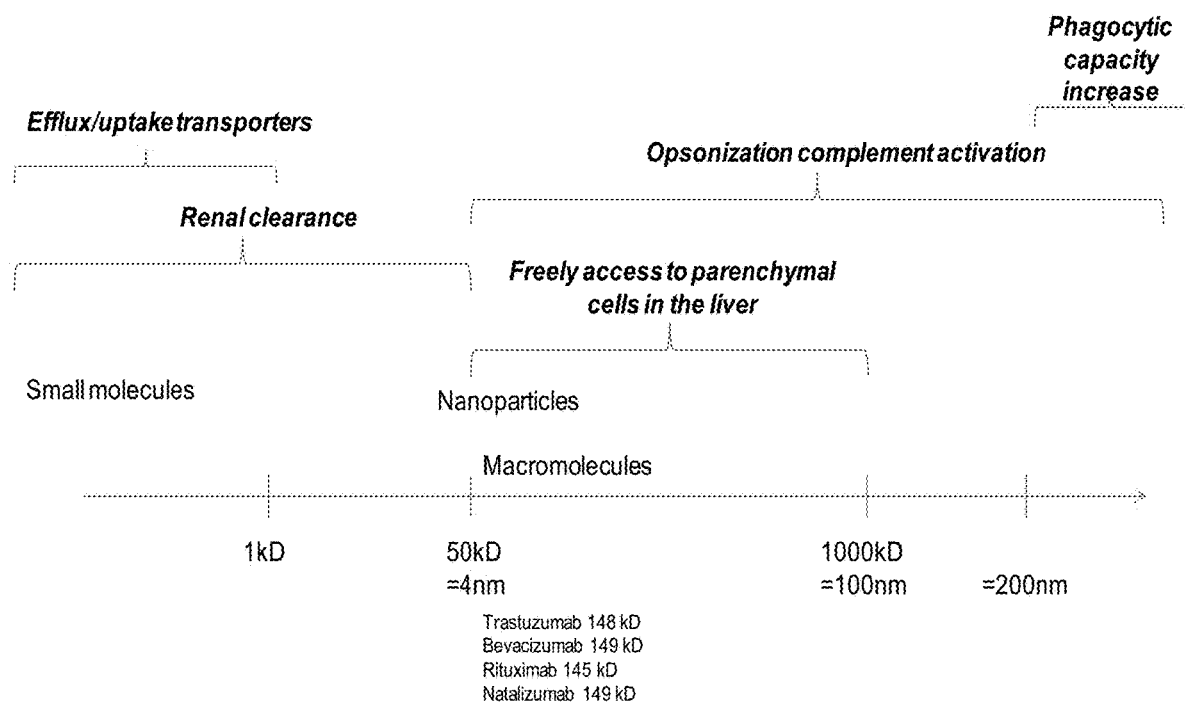
FIG. 1: Schematic view of possible routes for therapeutic compounds removal from blood circulation depending on the compound's size (longest dimension).

Example 1: Synthesis No. 1 of Liposomes as Biocompatible Nanoparticles

Liposomes are prepared using the lipidic film re-hydration method:
a) Lipids are solubilized in chloroform. Chloroform is finally evaporated under a nitrogen flow. Re-hydration of the lipidic film with HEPES 20 mM and NaCl 140 mM at pH 7.4 is performed at 50° C., so that the lipidic concentration is 5 mM.

The following lipidic composition was used to prepare charged liposomes: DPPC

| (DiPalmitoylPhosphatidylCholine): | 86% | mol; | MPPC |
| (MonoPalmitoylPhosphatidylcholine): | 10% | mol; | DSPE-PEG |
| (DiStearylPhosphatidylEthanolamine-[methoxy(PolyElthyleneGlycol)-2000]): | 4% mol. | | | b) Freeze-thaw cycles are then performed 6 times, by successively plunging the sample into liquid nitrogen and into a water bath regulated at 50° C.

c) A thermobarrel extruder (LIPEX™ Extruder, Northern Lipids) was used to calibrate the size of the liposomes under controlled temperature and pressure. In all cases, extrusion was performed at 50° C., under a pressure of 10 bars.

Size distribution of the as-prepared liposomes was determined by dynamic light scattering (DLS) using a Zetasizer NanoZS (Malvern Instruments) with a 633 nm HeNe laser at an angle of 90° C. The liposome suspension was diluted 100 times in HEPES 20 mM and NaCl 140 mM at pH 7.4. Liposome size (i.e. hydrodynamic diameter) was equal to about 170 nm with a polydispersity index (PDI) equal to about 0.1.

As understandable by the skilled person, the desired surface charge was obtained thanks to the selected lipidic composition, and its value was confirmed by zeta potential measurement using a Zetasizer NanoZS (Malvern Instruments).

The liposomes were diluted 100 times in water and the pH of the resulting suspension was adjusted to pH 7.4. The liposome surface charge was equal to about −14 mV at pH 7.4.

Example 2: Method Allowing a Reduction of at Least 10% of the Dose of Therapeutic Compound to be Administered to a Subject for an Equivalent Therapeutic Efficacy Thereof in the Subject A pharmaceutical composition according to claim 1 comprising a biocompatible nanoparticle and an activable oxide nanoparticle for anti-cancer therapy (used as "the compound" or "pharmaceutical compound") which can generate electron and/or high energy photon when exposed to ionizing radiations such as X-rays, is administered to nude mice bearing a xenografted tumor in the following manner:
a) administering to each nude mouse (by intravenous injection) the biocompatible nanoparticles;
b) between more than 5 minutes and 72 hours following step a), administering (by intra venous injection) the therapeutic compound to each mouse of step a) at a lower dose (10%) when compared to the dose currently used;
c) measuring the therapeutic compound concentration in blood or plasma samples of each mouse to obtain the pharmacokinetic parameters of the therapeutic compound, said concentration being measured once or preferably several times between 1 minute and 24 hours following the therapeutic compound administration;
d) assessing any clinical sign of toxicity after the administration of the pharmaceutical composition; and
e) measuring the tumor accumulation of the therapeutic compound 24 hours after its intravenous (IV) administration.

Example 3: Synthesis No. 2 of Liposomes as Biocompatible Nanoparticles

Liposomes are prepared using the lipid film re-hydration method:
a) Lipids are solubilized in chloroform. Chloroform is finally evaporated under a nitrogen flow. Re-hydration of the lipid film with HEPES 20 mM and NaCl 140 mM at pH 7.4 is performed at 60° C., so that the lipid concentration is 25 mM.

The following lipid composition was used to prepare charged liposomes: DPPC (DiPalmitoylPhosphatidylCholine) 62% mol; HSPC (Hydrogenated Soybean Phosphatidylcholine) 20% mol; CHOL (Cholesterol) 16% mol; POPS (1-Palmitoyl-2-Oleoyl Phosphatidyl Serine) 1% mol; DSPE-PEG (Di StearylPhosphatidylEthanolamine-[methoxy(PolyElthyleneGlycol)-2000]) 1% mol.

b) Freeze-thaw cycles are then performed 6 times, by successively plunging the sample into liquid nitrogen and into a water bath regulated at 60° C.

c) A thermobarrel extruder (LIPEX Extruder, Northern Lipids) was used to calibrate the size of the liposomes under controlled temperature and pressure. In all cases, extrusion was performed at 60° C., under a pressure of 5 bars, with a 0.1 μm pore size polyvinylidene fluoride (PVDF) membrane.

Size distribution of the as-prepared liposomes was determined by dynamic light scattering (DLS) using a Zetasizer NanoZS (Malvern Instruments) with a 633 nm HeNe laser at an angle of 90° C. The liposome suspension was diluted 100 times in HEPES 20 mM and NaCl 140 mM at pH 7.4. Liposome size (i.e. hydrodynamic diameter) was equal to about 145 nm with a polydispersity index (PDI) equal to about 0.1.

As understandable by the skilled person, the desired surface charge was obtained thanks to the selected lipidic composition, and its value was confirmed by zeta potential measurement using a Zetasizer NanoZS (Malvern Instruments).

The liposomes were diluted 100 times in a sodium chloride solution at 1 mM and the pH of the resulting suspension was adjusted to pH 7.4. The liposomes' surface charge was equal to about −25 mV at pH 7.4, NaCl 1 mM.

Figure 2:
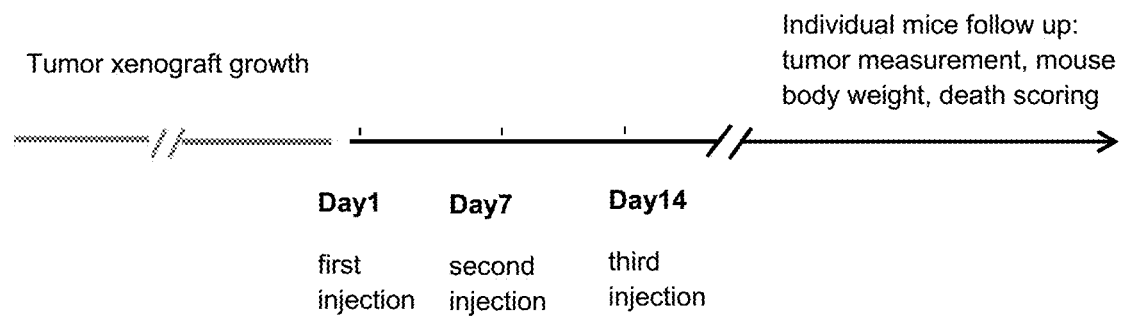
FIG. 2: Schematic representation of the treatment schedule for the pharmaceutical composition comprising (i) the biocompatible nanoparticles of Example 3 and (ii) the Dox-NP® in MDA-MB-231-lucD3H2LN xenografts.
Figure 3:
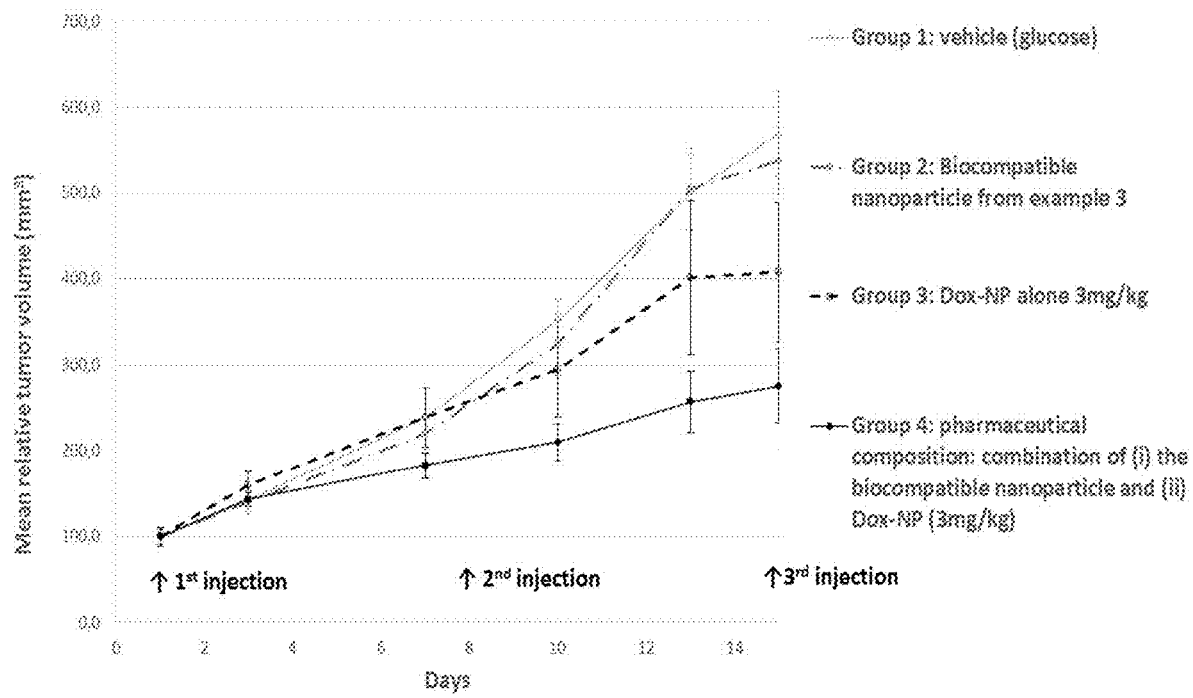
FIG. 3: Tumor re-growth delay of the pharmaceutical composition comprising the biocompatible nanoparticles of Example 3 and the Dox-NP® in MDA-MB-231-lucD3H2LN xenografts (mean RTV±SD).

Example 4: Tumor Re-Growth Delay of the Pharmaceutical Composition Comprising the Biocompatible Nanoparticle Suspension of Example 3 and the Dox-NP® in MDA-MB-231-lucD3H2LN Xenografts (FIGS. 2 and 3)

This study was performed to investigate the efficacy of the pharmaceutical composition comprising (i) the biocompatible nanoparticle from Example 3 and (ii) Dox-NP® (Liposomal Encapsulated Doxorubicin) as the therapeutic compound of interest, in MDA-MB-231-luc-D3H2LN tumor model xenografted on NMRI nude mice.

The human breast adenocarcinoma MDA-MB-231-luc-D3H2LN cell line was purchased from Caliper Life Science (Villepinte, France). The cells were cultured in Minimum Essential Medium with Earle's Balanced Salt Solution (MEM/EBSS) medium supplemented with 10% fetal bovine serum, 1% non-essential amino acids, 1% L-glutamine, and 1% sodium pyruvate (Gibco).

NMRI nude mice, 6-7 weeks (20-25 g) were ordered from Janvier Labs (France). Mice were subjected to a total body irradiation of 3Gy with the Cesium-137 irradiation device one day before the inoculation of the cancer cells for xenograft.

MDA-MB-231-luc-D3H2LN tumors were obtained by subcutaneous injection of $4 \times 10^6$ cells in 50 μL in the lower right flank of the mouse. The tumors were grown until reaching a volume around about 100 mm³. Tumor diameter was measured using a digital caliper and the tumor volume in mm³ was calculated using the formula:

$$\text{Tumor volume (mm}^3) = \frac{\text{length (mm)} \times (\text{width})^2 (\text{mm}^2)}{2}$$

Mice were randomized into separate cages and identified by a number (paw tattoo). Four groups were treated as illustrated in FIG. 2.

Group 1: Sterile Glucose 5% (Control (Vehicle) Group)

Four (4) mice were intravenously (IV) injected with a sterile glucose 5% solution on day 1, day 7 and day 14. Each time (day), two injections of glucose 5% were performed. The first injection of glucose 5% solution was performed 4 hours before the second injection.

Group 2: Biocompatible Nanoparticles from Example 3 (Control Group)

Four (4) mice were intravenously (IV) injected with a sterile glucose 5% solution and the biocompatible nanoparticles from Example 3 (10 ml/kg) on day 1, day 7 and day 14. Each time (day), the injection of biocompatible nanoparticles from Example 3 was performed 4 hours before injection of the glucose 5% solution.

Group 3: Dox-NP® (3 mg/kg Doxorubicin) (Treatment Group)

Five (5) mice were intravenously (IV) injected with a sterile glucose 5% solution and Dox-NP® (3 mg/kg doxorubicin) on day 1, day 7 and day 14. Each time (day), the injection of sterile glucose 5% solution was performed 4 hours before the injection of Dox-NP® (3 mg/kg doxorubicin).

Group 4: Pharmaceutical Composition, i.e. the Combination of (i) the Biocompatible Nanoparticles from Example 3 and of (ii) Dox-NP® (3 mg/kg Doxorubicin) (Treatment Group)

Five (5) mice were intravenously (IV) injected with the biocompatible nanoparticles from Example 3 (10 ml/kg) and with the Dox-NP® (3 mg/kg doxorubicin) on day 1, day 7 and day 14. Each time (day), the injection of biocompatible nanoparticles from Example 3 was performed 4 hours before the injection of Dox-NP® (3 mg/kg doxorubicin).

The Dox-NP® (Avanti Polar Lipids; liposomal formulation of 2 mg/ml doxorubicin HCl at pH 6.5-6.8, in 10 mM histidine buffer, with 10% w/v sucrose) was injected without additional dilution at a volume required to obtain 3 mg/kg of injected doxorubicin.

The biocompatible nanoparticle suspension from Example 3 was used without any additional dilution.

The Dox-NP® and the biocompatible nanoparticles from Example 3 were administrated by intravenous injection (IV) via lateral tail vein with a 100 U (0.3 ml) insulin syringe (Terumo, France).

Mice were followed up for clinical signs, body weight and tumor size.

The tumor volume was estimated from two dimensional tumor volume measurements with a digital caliper using the following formula:

$$\text{Tumor volume (mm}^3) = \frac{\text{length (mm)} \times (\text{width})^2 (\text{mm}^2)}{2}$$

In each group, the relative tumor volume (RTV) was expressed as $V_t/V_0$ ratio ($V_t$ being the tumor volume on a given day during the treatment and $V_0$ being the tumor volume at the beginning of the treatment).

The treatment efficacy was determined using the specific growth delay (SGD) over two doubling times (one doubling time being the amount of time it takes for the tumor to double in volume) and the optimal percent T/C value (% T/C).

The SGD was calculated over two doubling times as follows:

$$SGD = \frac{T4d \text{ treated} - T4d \text{ control}}{T4d \text{ control}}$$

with T4d being the time required for the tumor to double twice in volume (mean RTV from 100 mm³ up to 400 mm³).

The Percent T/C value ("% T/C") was calculated by dividing the median of the relative tumor volume of treated groups (groups 2, 3, 4) versus control group (group 1) at days 1, 3, 7, 10, 13, 15, 18, 21 and 24, and by multiplying the result of said division by 100 (see Table 2). The lowest % T/C values obtained within 2 weeks following treatment injection (with or without biocompatible nanoparticles as used in the context of the present invention) correspond to the optimal % T/C values.

FIG. 3 shows the mean relative tumor volume (mean RTV) for all groups as obtained (in the conditions previously described) after IV injections of:
- vehicle (sterile glucose 5%) on days 1, 7 and 14 (group 1);
- biocompatible nanoparticles from Example 3, 4 hours prior to each vehicle (sterile glucose 5%) injection on days 1, 7 and 14 (group 2);
- Dox-NP® (3 mg/kg doxorubicin) on days 1, 7 and 14 (group 3); or
- biocompatible nanoparticles from Example 3, 4 hours prior to the Dox-NP® (3 mg/kg doxorubicin) injection on days 1, 7 and 14 (group 4).

As shown in FIG. 3, a marked tumor growth inhibition is observed after the first injection of the pharmaceutical composition comprising the combination of (i) the biocompatible nanoparticles from Example 3 and (ii) the Dox-NP® (3 mg/kg doxorubicin), when compared to the Dox-NP® (3 mg/kg doxorubicin) alone.

The time required (expressed in days) for each tumor to double twice in volume (T4d) was calculated (as a measurement of the duration of the treatment effects). T4d for the pharmaceutical composition was estimated to about 31 days versus about 14 days for the Dox-NP® alone (Table 1). In addition the Specific Growth Delay (SGD) estimated from the tumors growth over two doubling time (starting from a mean RTV of 100 mm³ up to 400 mm³) was equal to about 2 for the pharmaceutical composition versus about 0 for the Dox-NP® alone (Table 1).

TABLE 1

Table 1: Time for the tumor to double twice in volume (T4d) and Specific Growth Delay (SGD) estimated from the tumors growth over two doubling times. Td4 represents the number of days to reach two doubling times (mean RTV from 100 mm³ up to 400 mm³). The control group is the vehicle (glucose 5%) alone (-).

| Groups | T4d (in days) between 100 and 400 mm³ (mean RTV) | SGD |
|---|---|---|
| Group 1: vehicle (control group) | 11 | — |
| Group 2: Biocompatible nanoparticles from Example 3 | 11 | 0 |
| Group 3: Dox-NP ® alone (3 mg/Kg) | 14 | 0 |
| Group 4: Pharmaceutical composition comprising (i) the biocompatible nanoparticle from Example 3 and (ii) Dox-N ® (3 mg/Kg) | 31 | 2 |

Furthermore, the percent T/C (% T/C) (calculated until the day of sacrifice of group 1) decreased faster for the pharmaceutical composition than for Dox-NP® alone. This demonstrates a marked impact of the pharmaceutical composition. The optimal % T/C of 25 observed at day 24 was indeed obtained for the pharmaceutical composition, i.e. the combination of (i) the biocompatible nanoparticles from Example 3 and (ii) the Dox-NP® (3 mg/kg doxorubicin), whereas the optimal % T/C of 38 observed at day 21 was obtained for the group Dox-NP® alone (Table 2).

TABLE 2

Table 2: percent T/C (% T/C) is calculated by dividing the median of the relative tumor volume of treated groups (groups 2, 3, 4) versus control group (group 1) at days 1, 3, 7, 10, 13, 15, 18, 21 and 24, and by multiplying the result of said division by 100. Control group is group 1 (vehicle sterile glucose 5% alone). % T/C is calculated until day 24 which corresponds to the day of sacrifice of group 1 (control group). Optimal % T/C is indicated for each group as **.

| Days | Group 2: biocompatible nanoparticles alone | Group 3: Dox-NP ® alone (3 mg/kg) | Group 4: Pharmaceutical composition comprising (i) the biocompatible nanoparticle and (ii) Dox-NP ® (3 mg/Kg) |
|---|---|---|---|
| 1 | 100 | 100 | 100 |
| 3 | 104 | 126 | 121 |
| 7 | 90 | 106 | 80 |
| 10 | 87 ** | 76 | 60 |
| 13 | 103 | 80 | 55 |
| 15 | 98 | 74 | 45 |
| 18 | 98 | 56 | 43 |
| 21 | 87 | 38 ** | 33 |
| 24 | 98 | 40 | 25 ** |

Overall, those results showed an advantageous tumor growth delay when using the pharmaceutical composition of the present invention [corresponding to the combination of (i) the biocompatible nanoparticles from Example 3 and of (ii) the Dox-NP® (3 mg/kg doxorubicin)], which is not observed when the Dox-NP® (3 mg/kg doxorubicin) is used alone (i.e. in the absence of the biocompatible nanoparticles used in the context of the present invention). This tumor growth delay was observed when the biocompatible nanoparticles from Example 3 and the compound of interest (the Dox-NP®) were administered sequentially, the biocompatible nanoparticle being administered to the subjects 4 hours before the Dox-NP®.

Inventors are reproducing this experiment to confirm that the same result is observed so long as the compound of interest and the biocompatible nanoparticles are administered to the subject between more than 5 minutes and about 72 hours from each other.

We claim:

1. A method comprising a step of intravenously administering a pharmaceutical compound of interest to a subject in need thereof and a distinct step of intravenously administering a biocompatible nanoparticle to said subject, wherein the longest dimension of the biocompatible nanoparticle is between about 4 nm and about 500 nm, and the surface charge value of the biocompatible nanoparticle is a negative charge below −10 mV, said nanoparticle being intravenously administered to the subject between more than 5 minutes and about 72 hours before the pharmaceutical compound of interest, and the biocompatible nanoparticle is an organic nanoparticle free of an additional therapeutic, prophylactic or diagnostic agent, and wherein the combined intravenous administration of the biocompatible nanoparticle and the compound of interest maintains the therapeutic benefit of the compound of interest with reduced toxicity, or increases the therapeutic benefit of the compound of interest with equivalent or reduced toxicity for the subject when compared to therapeutic benefit and toxicity induced by the standard therapeutic dose of said compound of interest.

2. The method according to claim 1, wherein the nanoparticle is selected from a lipid-based nanoparticle, a protein-based nanoparticle, a polymer-based nanoparticle, a copolymer-based nanoparticle, a carbon-based nanoparticle, and a virus-like nanoparticle.

3. The method according to claim 1, wherein the nanoparticle is further covered with a biocompatible coating.

4. The method according to claim 1, wherein the combined intravenous administration of the biocompatible nanoparticle and the compound of interest allows for a reduction of at least 10% of the administered compound therapeutic dose when compared to the standard therapeutic dose of said compound of interest while maintaining the same therapeutic benefit with equivalent or reduced toxicity for the subject, or while increasing the therapeutic benefit with equivalent or reduced toxicity for the subject.

5. The method according to claim 1, wherein the nanoparticle is cleared from the subject to whom it has been administered within one hour and six weeks after its administration.

6. The method according to claim 1, wherein the compound of interest is an organic compound.

7. The method according to claim 6, wherein said organic compound is a biological compound, a small-molecule targeted therapeutic, or a cytotoxic compound.

8. The method according to claim 6, wherein the compound of interest is selected from an antibody, an oligonucleotide, and a synthesized peptide.

9. The method according to claim 1, wherein the compound of interest is an inorganic compound selected from a metallic nanoparticle, a metal oxide nanoparticle, a metal sulfide nanoparticle or any mixture thereof.

10. The method according to claim 1, wherein the compound of interest is encapsulated in a carrier.

11. The method according to claim 1, wherein the compound of interest is bound to a carrier.

12. The method according to claim 1, wherein the nanoparticle is administered to the subject between more than 5 minutes and about 24 hours before the pharmaceutical compound of interest.

13. The method according to claim 1, wherein the nanoparticle has a surface charge value below −12 mV.

14. The method according to claim 1, wherein the nanoparticle has a surface charge value below −15 mV.

* * * * *

UNITED STATES PATENT AND TRADEMARK OFFICE
CERTIFICATE OF CORRECTION

PATENT NO. : 11,357,724 B2
APPLICATION NO. : 16/554765
DATED : June 14, 2022
INVENTOR(S) : Agnès Pottier et al.

It is certified that error appears in the above-identified patent and that said Letters Patent is hereby corrected as shown below:

In the Specification

Column 4,
Line 42, "at least 10 mV mV|)" should read --at least 10 mV (|10 mV|)--.

Column 10,
Line 3, "at least 10 mV mV|)." should read --at least 10 mV (|10 mV|).--.

Signed and Sealed this
Twenty-first Day of March, 2023

Katherine Kelly Vidal
*Director of the United States Patent and Trademark Office*